US012746367B2

(12) United States Patent
Blanchard et al.

(10) Patent No.: US 12,746,367 B2
(45) Date of Patent: Sep. 29, 2026

(54) PERIPHERAL INTRAVENOUS CATHETER ASSEMBLY HAVING AN EXTENSION SET

(71) Applicant: Becton, Dickinson and Company, Franklin Lakes, NJ (US)

(72) Inventors: Curtis H Blanchard, Riverton, UT (US); Nathan Mitchell, Murray, UT (US); Cristian Clavijo, Lehi, UT (US); Megan Scherich, Salt Lake City, UT (US); Austin Jason McKinnon, Herriman, UT (US); David Myers, Draper, UT (US); Weston F. Harding, Lehi, UT (US); Tyler Warner, Bluffdale, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 532 days.

(21) Appl. No.: 16/551,384

(22) Filed: Aug. 26, 2019

(65) Prior Publication Data

US 2020/0078564 A1 Mar. 12, 2020

Related U.S. Application Data

(60) Provisional application No. 62/729,302, filed on Sep. 10, 2018.

(51) Int. Cl.
*A61M 25/06* (2006.01)
*A61B 5/15* (2006.01)
(Continued)

(52) U.S. Cl.
CPC .... *A61M 25/0606* (2013.01); *A61M 25/0097* (2013.01); *A61M 25/0693* (2013.01);
(Continued)

(58) Field of Classification Search
CPC .......... A61M 25/0606; A61M 25/0097; A61M 25/0693; A61M 2039/1088;
(Continued)

(56) References Cited

U.S. PATENT DOCUMENTS 4,034,754 A * 7/1977 Virag .................... A61M 39/08 604/122
4,197,847 A * 4/1980 Djerassi .............. A61M 1/3616 604/6.02
(Continued)

FOREIGN PATENT DOCUMENTS

CN 106620939 A 5/2017
JP 2011518024 A 6/2011
(Continued)

*Primary Examiner* — Chelsea E Stinson
*Assistant Examiner* — Hamza A Darb
(74) *Attorney, Agent, or Firm* — Kirton McConkie; Whitney Blair; Kevin Stinger

(57) ABSTRACT

A catheter assembly may include a catheter adapter, which may include a proximal end, a distal end, a lumen extending through the proximal end and the distal end, and a side port. The catheter assembly may include an extension set, which may include a first extension tube that may extend from the side port. The extension set may include a first connector, which may be coupled to a proximal end of the first extension tube. The first connector may include a first port and a second port. The extension set may also include a second extension tube. A distal end of the second extension tube may be coupled to the first port. The second extension tube may be longer than the first extension tube. The extension set may include a second connector, which may be coupled to the proximal end of the second extension tube.

15 Claims, 11 Drawing Sheets

(51) Int. Cl.
*A61M 25/00* (2006.01)
*A61M 39/10* (2006.01)

(52) U.S. Cl.
CPC ..... *A61B 5/15003* (2013.01); *A61B 5/150389* (2013.01); *A61B 5/150992* (2013.01); *A61M 2039/1077* (2013.01)

(58) Field of Classification Search
CPC .. A61M 2039/1077; A61M 2039/1083; A61M 39/10; A61B 5/15003; A61B 5/150389; A61B 5/150992; A61B 5/150221; A61B 5/150503
See application file for complete search history.

(56) References Cited

U.S. PATENT DOCUMENTS

| | | | | | |
|---|---|---|---|---|---|
| 5,078,688 | A * | 1/1992 | Lobodzinski | A61M 25/0606 | 604/167.05 |
| 8,412,300 | B2 | 4/2013 | Sonderegger | | |
| 2004/0267213 | A1* | 12/2004 | Knapp | A61B 17/0218 | 604/284 |
| 2006/0089604 | A1* | 4/2006 | Guerrero | A61M 5/1408 | 604/247 |
| 2006/0149350 | A1 | 7/2006 | Patel | | |
| 2006/0293560 | A1 | 12/2006 | Nguyen | | |
| 2008/0188831 | A1* | 8/2008 | Bonnette | A61M 25/0097 | 604/524 |
| 2009/0156983 | A1* | 6/2009 | Bonnette | A61B 17/32037 | 604/22 |
| 2009/0163985 | A1* | 6/2009 | Dave | A61F 2/958 | 623/1.11 |
| 2010/0204553 | A1 | 8/2010 | Sonderegger | | |
| 2014/0128823 | A1* | 5/2014 | Odland | A61B 5/150992 | 604/319 |
| 2016/0136398 | A1 | 5/2016 | Heilman et al. | | |
| 2017/0120011 | A1* | 5/2017 | Burkholz | A61M 25/0097 | |
| 2017/0120016 | A1* | 5/2017 | Burkholz | A61M 25/0637 | |
| 2017/0239443 | A1 | 8/2017 | Abitabilo et al. | | |
| 2018/0050177 | A1* | 2/2018 | Yamashita | A61M 25/008 | |
| 2018/0326185 | A1* | 11/2018 | Cline | A61M 25/0662 | |

FOREIGN PATENT DOCUMENTS

| | | | |
|---|---|---|---|
| JP | 2012517328 | A | 8/2012 |
| JP | 2013529116 | A | 7/2013 |
| WO | 92/13584 | | 8/1992 |
| WO | 2009/117663 | | 9/2009 |
| WO | 2017143176 | A1 | 8/2017 |

* cited by examiner

PERIPHERAL INTRAVENOUS CATHETER ASSEMBLY HAVING AN EXTENSION SET

RELATED APPLICATIONS

This application claims the benefit of U.S. Provisional Application No. 62/729,302, filed Sep. 10, 2018, and entitled PERIPHERAL INTRAVENOUS CATHETER ASSEMBLY HAVING AN EXTENSION SET, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and introducer needle are generally inserted at a shallow angle through the skin into vasculature of the patient.

In order to verify proper placement of the introducer needle and/or the PIVC in the blood vessel, a clinician generally confirms that there is "flashback" of blood in a flashback chamber of a PIVC assembly. Once placement of the needle has been confirmed, the clinician may temporarily occlude flow in the vasculature and remove the introducer needle, leaving the PIVC in place for future blood withdrawal and/or fluid infusion. The PIVC assembly may be coupled with an extension set, which may allow coupling of an infusion or blood withdrawal device at a location removed from an insertion site of the PIVC.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to devices, systems, and methods for facilitating delivery of an instrument and/or fluid through a catheter, which may include a peripheral intravenous catheter (PIVC). The devices, systems, and methods of the present disclosure may also be used for blood withdrawal, according to some embodiments. In some embodiments, the instrument may include an additional catheter for fluid infusion or blood draw, a guidewire, a probe with a sensor, or a light tube for disinfection.

In some embodiments, a catheter assembly may include a catheter adapter. In some embodiments, the catheter adapter may include a proximal end, a distal end, a lumen extending through the proximal end and the distal end, and a side port. In some embodiments, the catheter assembly may include a catheter, such as, for example, a PIVC, which may extend distally from the catheter adapter.

In some embodiments, the catheter assembly may include a first extension tube, which may include a proximal end and a distal end. In some embodiments, the first extension tube may extend from the side port. In some embodiments, the catheter assembly may include a first connector coupled to the proximal end of the first extension tube. In some embodiments, the first connector may include a first port and/or a second port.

In some embodiments, the catheter assembly may include a second extension tube, which may include a proximal end and a distal end. In some embodiments, the distal end of the second extension tube may be coupled to the first port. In some embodiments, the second extension tube may be longer than the first extension tube. In some embodiments, the catheter assembly may include a second connector coupled to the proximal end of the second extension tube. In some embodiments, a clamp may be disposed on the first extension tube and/or the second extension tube.

In some embodiments, the first port may direct the second extension tube distally. In some embodiments, the first port may be disposed at an angle of less than 90° with respect to the second port. In some embodiments, the second port may be aligned with a longitudinal axis of the first connector. In some embodiments, the first port may be disposed at an angle between 45° and 90° with respect to the second port. In some embodiments, the first port may be perpendicular to the second port.

In some embodiments, the first connector may include a Y-shape or a T-shape. In some embodiments, the first port and the second port may form arms of the Y-shape or the T-shape. In some embodiments, the first connector may include a third port, which may form a trunk of the Y-shape or the T-shape. In some embodiments, the third port may extend proximally, and the first port and the second port may extend distally. In some embodiments, the first port may direct the second extension tube across a longitudinal axis of the catheter adapter.

In some embodiments, the first connector may not include any catch points for fluid or the instrument moving through the first connector in a distal direction to enter the catheter adapter. In some embodiments, the second connector may not include any catch points for fluid or the instrument moving through the second connector in the distal direction.

In some embodiments, the first connector may be selectively coupled to the first extension tube. Alternatively, in some embodiments, the first connector may be permanently or non-removably coupled to the first extension tube. In some embodiments, the proximal end of the first extension tube may be fixed within the first connector. In some embodiments, the first connector may be coupled to the proximal end of the first extension tube via a snap fit.

In some embodiments, the catheter adapter may include multiple side ports. In some embodiments, the side port may be a first side port, and the catheter adapter may include a second side port. In some embodiments, the second side port may oppose the first side port or extend from a top of the catheter adapter. In some embodiments, the catheter assembly may include one or more of the following: a third extension tube, a third connector, a fourth extension tube, and a fourth connector.

In some embodiments, the third extension tube may include a proximal end and a distal end. In some embodiments, the third extension tube may extend from the second side port. In some embodiments, the third connector may be coupled to the proximal end of the third extension tube. In some embodiments, the third connector may include a third port and a fourth port. In some embodiments, the fourth extension tube may include a proximal end and a distal end.

In some embodiments, the distal end of the fourth extension tube may be coupled to the third port of the third connector. In some embodiments, the fourth extension tube may be longer than the third extension tube. In some embodiments, the fourth connector may be coupled to the proximal end of the fourth extension tube. Thus, in some embodiments, the catheter assembly may include multiple extension sets.

In some embodiments, the third extension tube may extend from the distal end of the catheter adapter. In some embodiments, the distal end of the catheter adapter may include a needle port and/or a distal port from which the third extension tube extends. In some embodiments, the needle port and the distal port may be disposed vertically with respect to each other. In some embodiments, the needle port and the distal port may be disposed horizontally with respect to each other.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
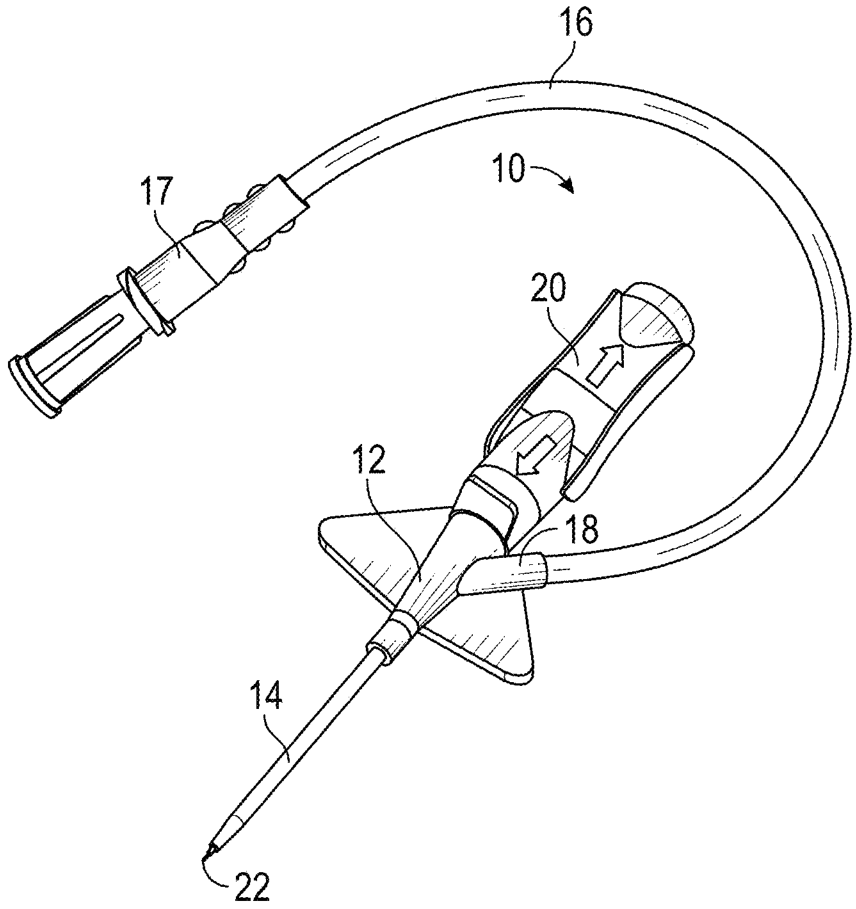
FIG. 1A (Prior Art)
FIG. 1A is an upper perspective view of an example prior art catheter assembly.
Figure 1B:
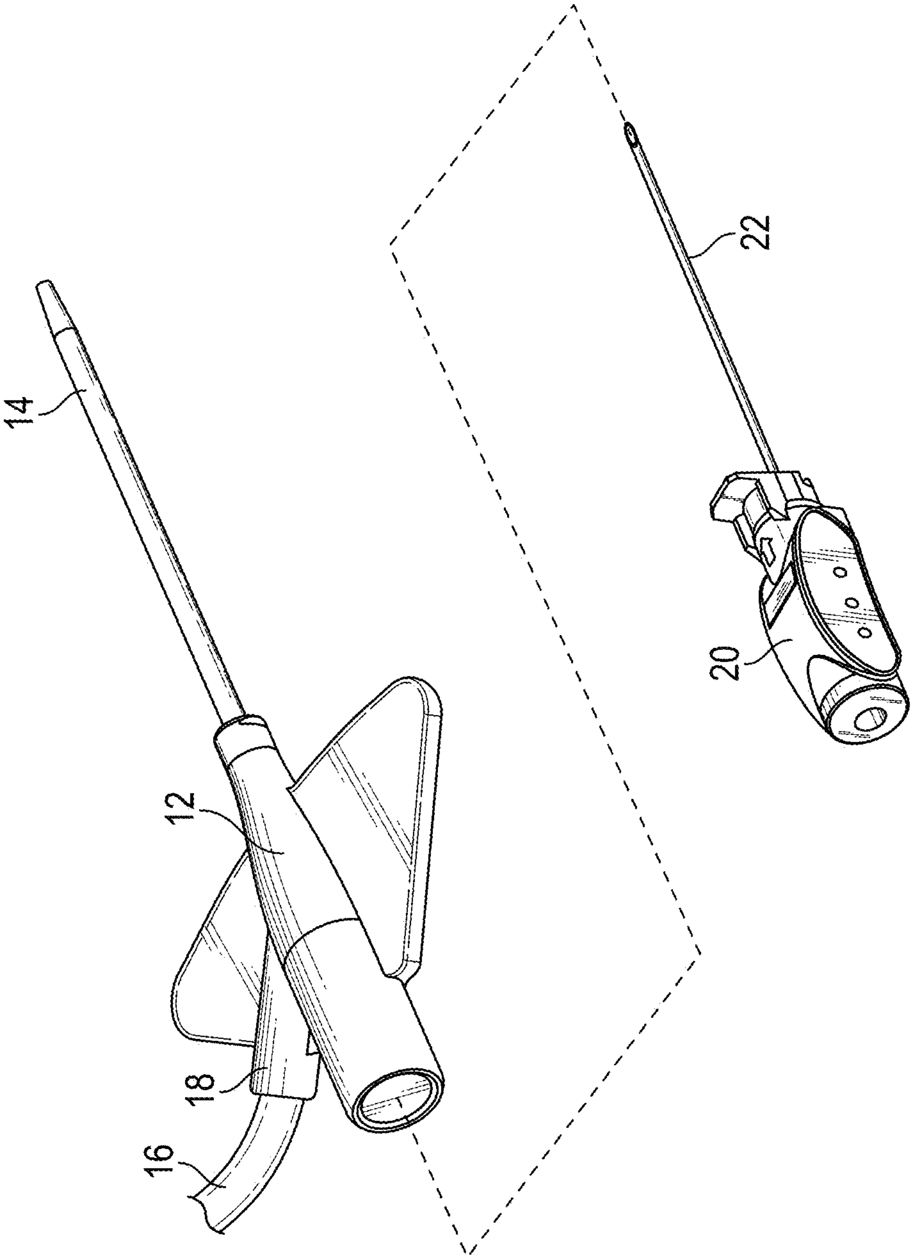
FIG. 1B (Prior Art)
FIG. 1B is an upper perspective view of a prior art needle assembly removed from the prior art catheter assembly.

Referring now to FIGS. 1A-1B, a prior art catheter assembly 10 is illustrated. The prior art catheter assembly 10 includes a catheter adapter 12 and a catheter 14 extending distally from the catheter adapter 12. The prior art catheter assembly 10 also includes an extension set, which includes an extension tube 16 and a connector 17. The extension tube 16 extends from a side port 18 of the catheter adapter 12.

The prior art catheter assembly 10 further includes a needle hub 20 and an introducer needle 22. When the needle hub 20 is coupled to the catheter adapter 12, the introducer needle 22 extends through the catheter adapter 12 and the catheter 14 and beyond a distal end of the catheter 14 to aid in insertion of the catheter 14 into vasculature of a patient.

As illustrated in FIG. 1A, the extension tube 16 may curve around a proximal end of the catheter adapter 12 and/or the needle hub 20. In these and other instances, the extension tube 16 may be in the way of a hand of a clinician as the clinician attempts to insert the catheter 14 into the vasculature of the patient. In some instances, the clinician may grip the extension set in his or her fingers to control the extension set during insertion of the catheter 14 into the vasculature of a patient and/or to prevent the extension set from contacting an insertion site of the catheter 14 once the catheter 14 is inserted into the vasculature of the patient. Gripping the extension set in such a way during insertion of the catheter 14 may be complicated and require physical coordination of the clinician. Furthermore, in some instances, the extension tube 16 and/or the connector 17 may interfere with visualization of blood flashback by the clinician.

Figure 1C:
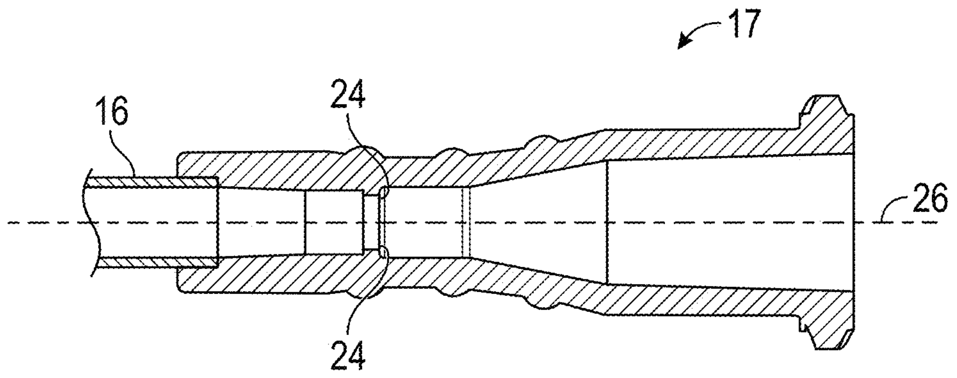
FIG. 1C (Prior Art)
FIG. 1C is a cross-sectional view of an example prior art connector.

Referring now to FIG. 1C, the connector 17 of the prior art catheter assembly 10 includes one or more catch points 24, which may interfere with fluid or a probe moving in a distal direction through the connector 17. In some instances, the catch points 24 may include surfaces generally perpendicular to a longitudinal axis 26 or flow path of the connector 17.

Figure 2A:
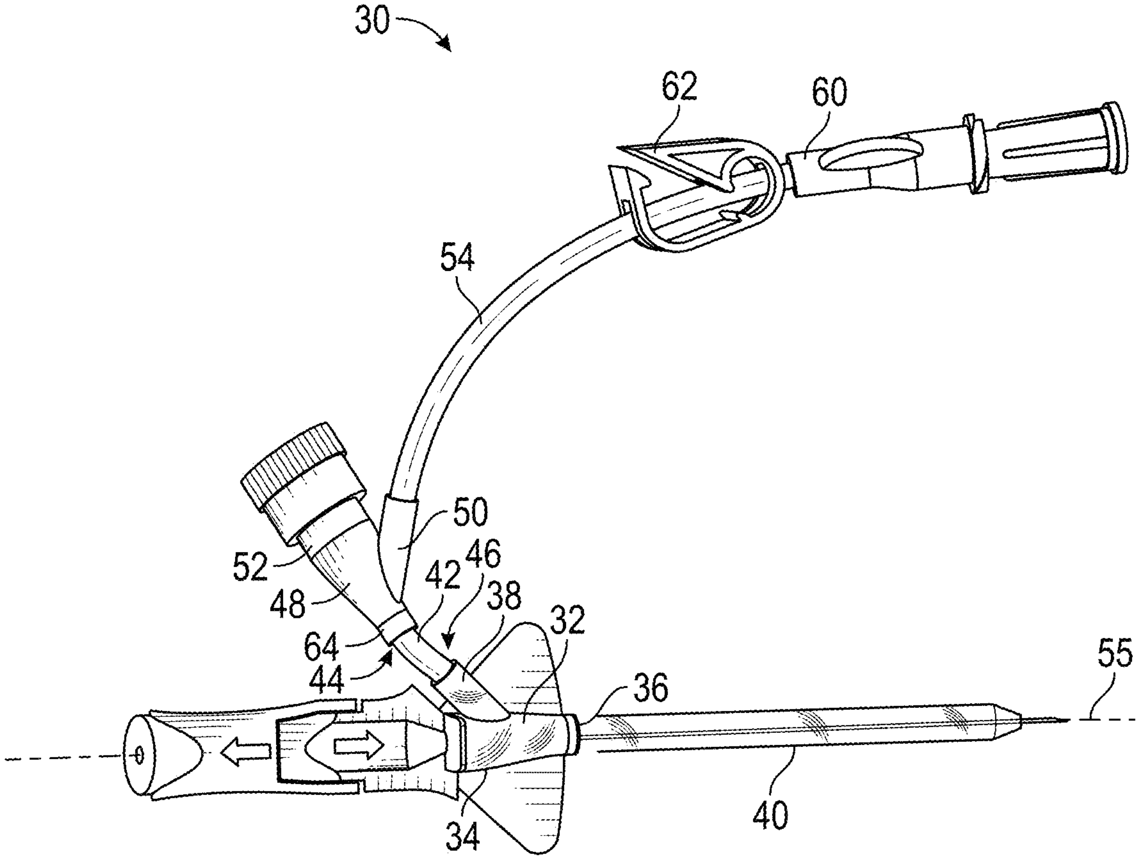
FIG. 2A is an upper perspective view of a catheter assembly having an example Y-shaped connector, according to some embodiments.
Figure 2B:
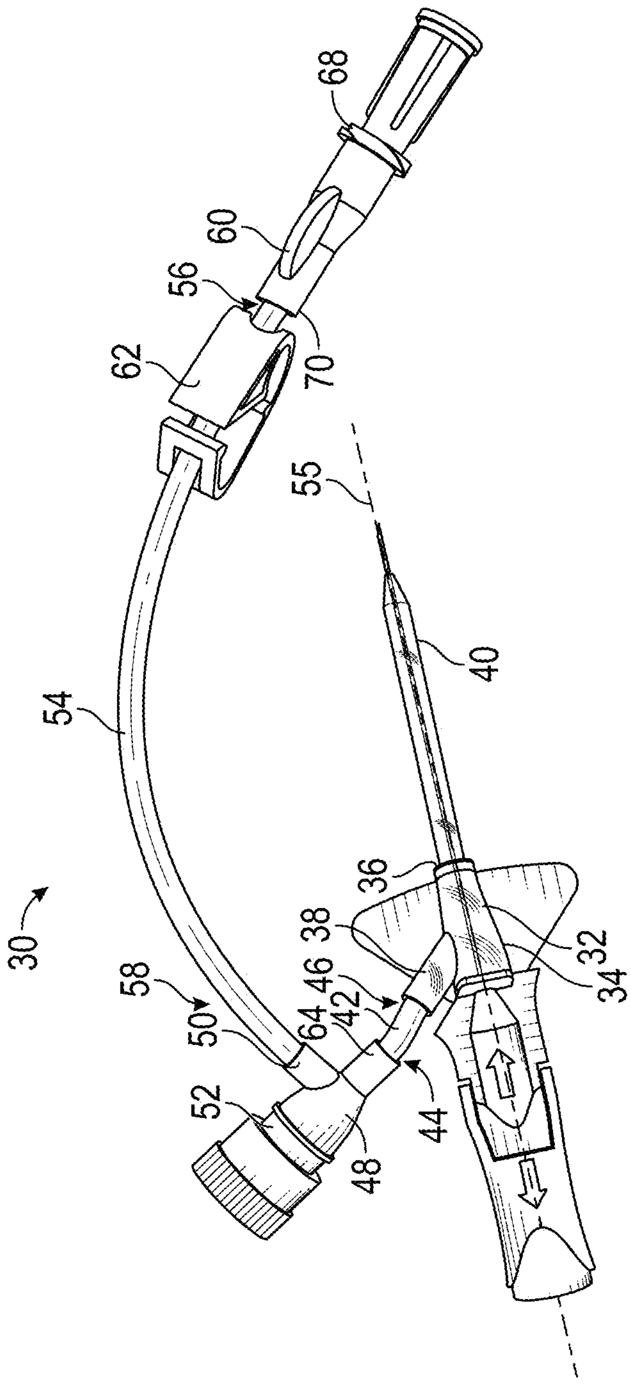
FIG. 2B is an upper perspective view of the catheter assembly of FIG. 2A having an example T-shaped connector, according to some embodiments.

Referring now to FIGS. 2A-2B, in some embodiments, a catheter assembly 30 may include a catheter adapter 32, which may include a proximal end 34, a distal end 36, a lumen extending through the proximal end 34 and the distal end 36, and a side port 38. In some embodiments, the catheter assembly 30 may include a catheter 40, such as, for example, a PIVC, extending distally from the catheter adapter 32. In some embodiments, the catheter assembly 30 may include one or more elements of the prior art catheter assembly 10.

In some embodiments, the catheter assembly 30 may include a first extension tube 42, which may include a proximal end 44 and a distal end 46. In some embodiments, the first extension tube 42 may extend from the side port 38. In some embodiments, the catheter assembly 30 may include a first connector 48 coupled to the proximal end 44 of the first extension tube 42. In some embodiments, the first connector 48 may include a first port 50 and a second port 52. In some embodiments, the first connector 48 and/or the second port 52 may be disposed in proximity to the catheter adapter 32 and the catheter 40 to improve access for an instrument, as well as to allow higher viscosity or speed-critical fluid injections and improved flushing. In some embodiments, the instrument may include an additional catheter for fluid infusion or blood draw, a guidewire, a probe with a sensor, or a light tube for disinfection. In some embodiments, a length of the first extension tube 42 may be about 12 millimeters. In some embodiments, the length of the first extension tube 42 may be between about 11 and 13 millimeters. In some embodiments, the length of the first extension tube 42 may be between about 10 and 14 millimeters. In some embodiments, the length of the first extension tube 42 may be greater than 12 millimeters. In some embodiments, the length of the first extension tube 42 may be less than 12 millimeters. The length of the first extension tube 42 may vary, according to some embodiments.

In some embodiments, the catheter assembly 30 may include a second extension tube 54, which may include a proximal end 56 and a distal end 58. In some embodiments, the distal end 58 of the second extension tube 54 may be coupled to the first port 50. In some embodiments, the second extension tube 54 may be longer than the first extension tube 42. In some embodiments, the catheter assembly 30 may include a second connector 60, which may be coupled to the proximal end 56 of the second extension tube 54. In some embodiments, the second port 52 may be aligned with a longitudinal axis of the first connector 48. In some embodiments, a clamp 62, such as, for example, a slide clamp or a pinch clamp, may be disposed on the first extension tube 42 and/or the second extension tube 54.

In some embodiments, the first port 50 may direct the second extension tube 54 distally. In some embodiments, the second extension tube 54 may be disposed away from an area behind the catheter adapter 32 and away from a longitudinal axis 55 of the catheter adapter 32 to prevent interference of the second extension tube 54 with the hand of the clinician as the clinician grips the catheter adapter 32 to insert the catheter 40 into the vasculature of the patient. In some embodiments, the combined angles of the first port 50 and the side port 38 of the catheter adapter 32 relative to the longitudinal axes of the first connector 48 and the catheter adapter 32 respectively may be selected to cause the first port 50 to be oriented substantially perpendicular to the longitudinal axis of the catheter adapter 32 as is shown in FIG. 2A. In the claims, the term "substantially perpendicular" shall mean between 85° and 95°. The term "approximately" shall mean the stated value ±5%. In some embodiments, the combined angles of the first port 50 and the side port 38 of the catheter adapter 32 may be selected to cause the first port 50 to be oriented at an angle greater than 90° to the longitudinal axis of the catheter adapter 32 such that the first port 50 is oriented distally as is shown in FIG. 2B.

In some embodiments, the first port 50 may be disposed at an angle of less than 90° with respect to the second port 52, as illustrated, for example, in FIG. 2A. In further detail, in some embodiments, the first port 50 may be disposed at an angle between 45° and 90° with respect to the second port 52. In some embodiments, the first port 50 may be perpendicular to the second port 52, as illustrated, for example, in FIG. 2B. In some embodiments, an increased angle between the first port 50 and the second port 52 may facilitate flushing of the first port 50 without flushing the second port 52. In some embodiments, a decreased angle between the first port 50 and the second port 52 may streamline fluid flow and instrument delivery into the catheter 40. In some embodiments, streamlined fluid flow may be beneficial for infusion of highly viscous medications or medications that are time-dependent.

In some embodiments, an extension set may include one or more of the following: the first extension tube 42, the first connector 48, the second extension tube 54, and the second connector 60. In some embodiments, the second extension tube 54 may be shorter than the extension tube 16 of the prior art, which may result in less movement of the extension set and fewer problems in controlling the extension set. However, in some embodiments, the second connector 60 may be disposed about a same distance from the insertion site as the connector 17 of the prior art, which may decrease interference with the catheter 40 at the insertion site. In some embodiments, a length of the second extension tube 54 may be less than about 5.350 inches. In some embodiments, the length of the second extension tube 54 may be between about 4 and 7 inches. In some embodiments, the length of the second extension tube 54 may be less than about 6 inches or less than about 5.350 inches. The length of the second extension tube 54 may vary, according to some embodiments.

In some embodiments, the first connector 48 may include a Y-shape or a T-shape. In some embodiments, the first port 50 and the second port 52 may form arms of the Y-shape. In some embodiments, the first connector 48 may include a third port 64, which may form a trunk of the Y-shape.

In some embodiments, the first connector 48 may be selectively coupled to the first extension tube 42 and/or the second extension tube 54. In some embodiments, the first connector 48 may be permanently or non-removably coupled to the first extension tube 42 and/or the second extension tube 54. In some embodiments, the first port 50, the second port 52, and the third port 64 of the first connector 48 may include any suitable type of coupling mechanism.

In some embodiments, one or more of the first port 50, the second port 52, and the third port 64 may include a luer adapter, such as, for example, a slip or thread male or female luer adapter. In some embodiments, one or more of the first port 50, the second port 52, and the third port 64 may include a non-luer adapter. In some embodiments, one or more of the first port 50, the second port 52, and the third port 64 may include a blunt plastic cannula, such as, for example, the Baxter Interlink IV Access System. In some embodiments, one or more of the first port 50, the second port 52, and the third port 64 may include one or more barbs.

In some embodiments, one or more of the first port 50, the second port 52, and the third port 64 may be coupled to a needleless connector, such as, for example, the Becton Dickinson SMARTSITE™ needle-free valve, or another suitable needleless connector. In some embodiments, one or more of the first port 50, the second port 52, and the third port 64 may be closed by an end cap. In some embodiments, one or more of the first port 50, the second port 52, and the third port 64 may include a vent plug. In some embodiments, one or more of the first port 50, the second port 52, and the third port 64 may include one or more snap elements, examples of which are illustrated in FIG. 7B.

In some embodiments, the distal end 58 of the second extension tube 54 may include a particular connector having a corresponding coupling mechanism to the first port 50. In some embodiments, the distal end 58 of the second extension tube 54 may be fixed inside the first connector 48. In some embodiments, the proximal end 44 of the first extension tube 42 may include a particular connector having a corresponding coupling mechanism to the third port 64 and/or the first port 50. In some embodiments, the proximal end 44 of the first extension tube 42 may be fixed inside the first connector 48, as illustrated, for example, in FIGS. 2A-2C.

In some embodiments, the catheter assembly 30 may not include the second extension tube 54 and/or the second connector 60. In some embodiments, the first connector 48 may only include the first port 50 and the third port 64, which may be disposed opposite the first port 50. In some embodiments, the first connector 48 may include more than three ports.

In some embodiments, the second connector 60 may be selectively coupled to the second extension tube 54. Alternatively, in some embodiments, the second connector 60 may be permanently or non-removably coupled to the second extension tube 54. In some embodiments, the second connector 60 may include multiple ports, which may each include any suitable type of coupling mechanism. For example, the second connector 60 may include a proximal port 68 and a distal port 70. In some embodiments, the second connector 60 may include a Y-shape or a T-shape.

In some embodiments, one or more of the multiple ports may include a luer adapter, such as, for example, a slip or thread male or female luer adapter. In some embodiments, one or more of the multiple ports may include a non-luer adapter. In some embodiments, one or more of the multiple ports may include a blunt plastic cannula, such as, for example, the Baxter Interlink IV Access System. In some embodiments, one or more of the multiple ports may include one or more barbs. In some embodiments, one or more of the multiple ports may be coupled to a needleless connector, such as, for example, the Becton Dickinson SMARTSITE™ needle-free valve, or another suitable needleless connector. In some embodiments, one or more of the one or more of the multiple ports may be closed by an end cap. In some embodiments, one or more of the multiple ports may include a vent plug. In some embodiments, one or more of the multiple ports may include one or more snap elements, examples of which are illustrated in FIG. 7B. In some embodiments, the proximal end 56 of the second extension tube 54 may include a particular connector having a corresponding coupling mechanism to the distal port 70. In some embodiments, the proximal end 56 of the second extension tube 54 may be fixed inside the second connector 60, as illustrated, for example, in FIGS. 2A-2C.

In some embodiments, the distal end 46 of the first extension tube 42 may be selectively coupled to the catheter adapter 32. Alternatively, in some embodiments, the distal end 46 of the first extension tube 42 may be permanently or non-removably coupled to the catheter adapter 32. In some embodiments, the distal end 46 of the first extension tube 42 may be fixed within the catheter adapter 32, as illustrated, for example, in FIGS. 2A-2C. In some embodiments, the side port 38 of the catheter adapter 32 may include a luer adapter, such as, for example, a slip or thread male or female luer adapter. In some embodiments, the side port 38 of the catheter adapter 32 may include a non-luer adapter. In some embodiments, the side port 38 of the catheter adapter 32 may include one or more snap elements, examples of which are illustrated in FIG. 7B. In some embodiments, the distal end 46 of the first extension tube 42 may include a particular connector having a corresponding coupling mechanism to the side port 38.

In some embodiments, the first extension tube 42 may be coupled to the catheter adapter 32 and/or the first connector 48 prior to or after insertion of the catheter 40 into the vasculature of the patient and/or removal of an introducer needle from the catheter assembly 30. In some embodiments, the second extension tube 54 may be coupled to the first connector 48 prior to or after insertion of the catheter 40 into the vasculature of the patient and/or removal of an introducer needle from the catheter assembly 30.

Figure 2C:
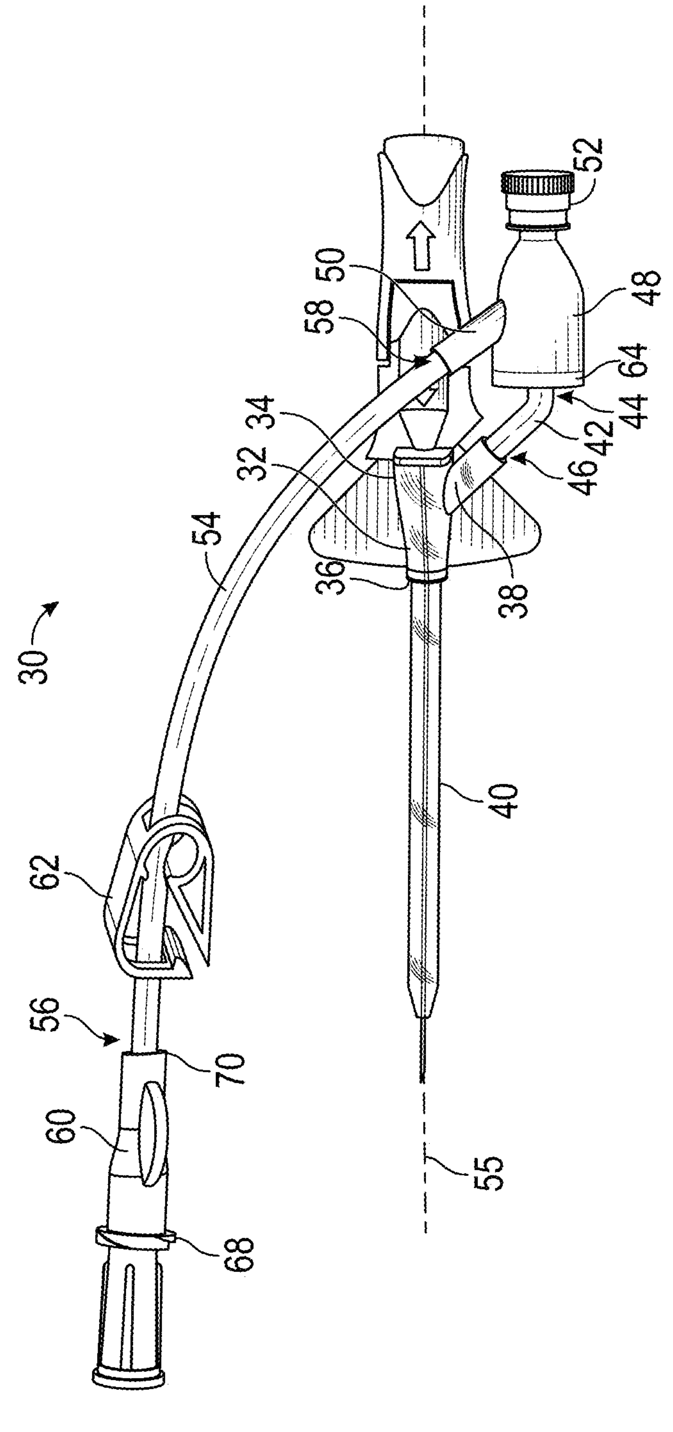
FIG. 2C is an upper perspective view of the catheter assembly of FIG. 2A having an example inverted Y-shaped connector, according to some embodiments.

Referring now to FIG. 2C, in some embodiments, the second port 52 may extend proximally, and the first port 50 and the third port 64 may extend distally. In some embodiments, the first port 50 may direct the second extension tube 54 across the longitudinal axis 55 of the catheter adapter 32. In some embodiments, the third port 64 may be coupled to the proximal end 44 of the first extension tube 42. In some embodiments, the first connector 48 and/or the second connector 60 may be transparent, which may facilitate access, flow, flush, and manufacturing visibility.

Figure 3A:
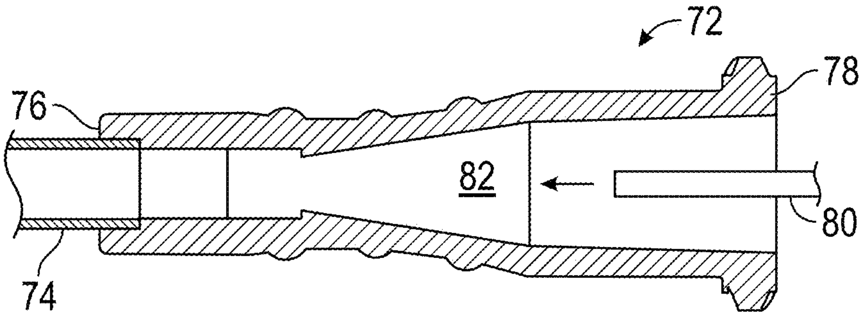
FIG. 3A is a cross-sectional view of an example connector, according to some embodiments.

Referring now to FIG. 3A, an example connector 72 is illustrated. In some embodiments, the connector 72 may include or correspond to the first connector 48 and/or the second connector 60 discussed with respect to FIGS. 2A-2B. In some embodiments, a proximal end of the extension tube 74 may be fixed within a distal port 76 of the connector 72. In some embodiments, the proximal end of the extension tube 74 may include or correspond to the proximal end 44 of the first extension tube 42 and/or the proximal end 56 of the second extension tube 54. In some embodiments, the distal port 76 may include or correspond to the distal port 70 of the second connector 60 and/or the third port 64 of the first connector 48. In some embodiments, a proximal port 78 of the connector 72 may include or correspond to the proximal port 68 of the second connector 60 and/or the second port 52 of the first connector 48.

In some embodiments, the connector 72 may not include any catch points for fluid or the instrument 80 moving through the connector 72 in the distal direction. For example, the catch points 24, illustrated in FIG. 1C, may be removed. In some embodiments, an entirety of a lumen 82 of the connector 72 tapers inwardly in the distal direction or expands to a larger diameter in the distal direction. In some embodiments, all portions of an inner surface of the connector 72 forming the lumen 82 that are perpendicular to a longitudinal axis of the connector 72 may be removed. In some embodiments, the connector 72 may or may not include a wedge to eliminate the catch points.

Figure 3B:
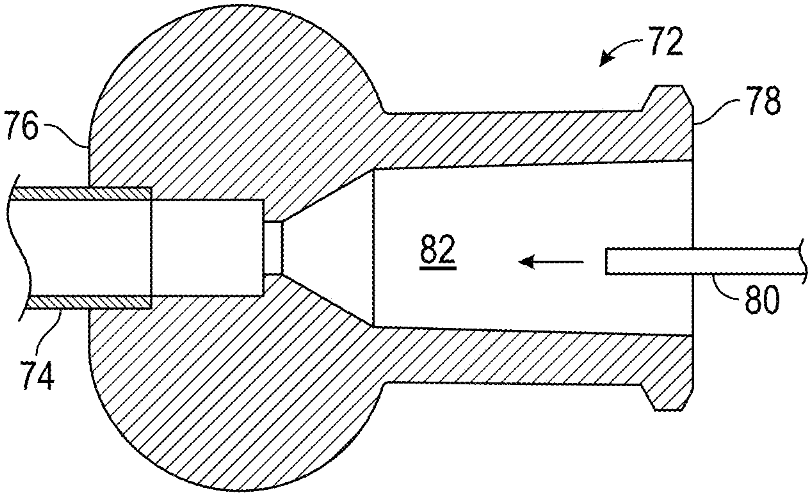
FIG. 3B is a cross-sectional view of another example connector, according to some embodiments.

Referring now to FIG. 3B, in some embodiments, the connector 72 may be shortened to facilitate rapid infusion of medications and instrument access. In some embodiments, a length of the connector 72 may be between about 0.5 and 0.6 inches. In some embodiments, the length of the connector 72 may be about 0.57 inches.

Figure 4A:
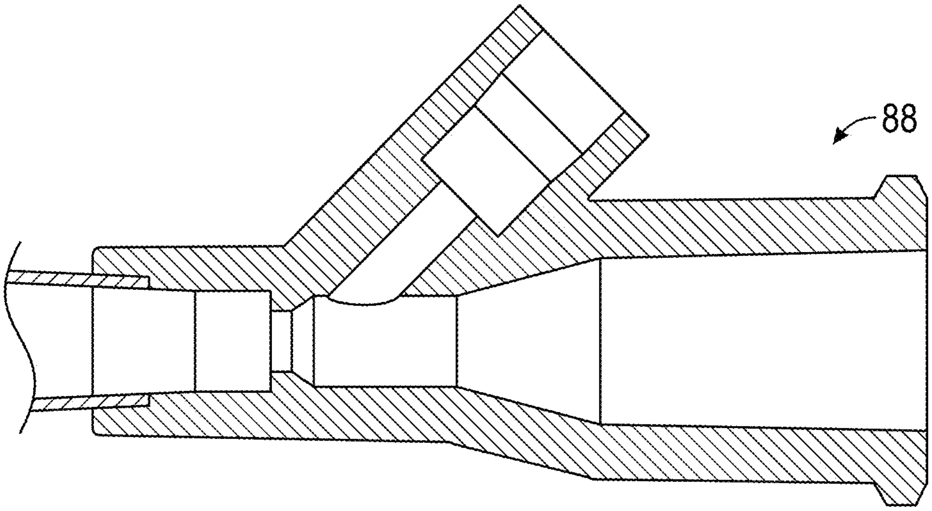
FIG. 4A is a cross-sectional view of an example Y-shaped connector, according to some embodiments.

Referring now to FIG. 4A, in some embodiments, another connector 88 is illustrated, according to some embodiments. In some embodiments, the connector 88 may include or correspond to the first connector 48 and/or the second connector 60 discussed with respect to FIGS. 2A-2B. In some embodiments, the connector 88 may not include any catch points for fluid or the instrument 80 (illustrated, for example, in FIGS. 3A-3B) moving through the connector 88 in the distal direction to enter the catheter adapter 32. In some embodiments, catch points similar to the catch points 24, illustrated in FIG. 1C, for example, may be removed from a fluid pathway between a proximal port and a distal port, or between the second port 52 and the third port 64 of FIGS. 2A-2B, for example. In some embodiments, the connector 88 may or may not include a wedge to eliminate the catch points.

Figure 4B:
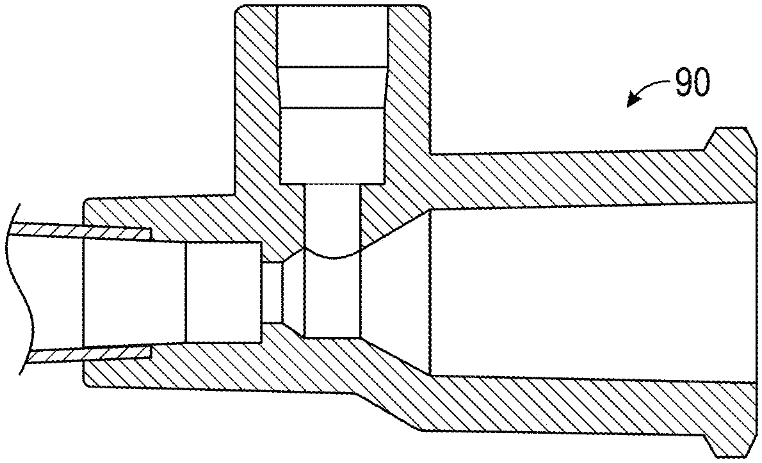
FIG. 4B is a cross-sectional view of an example T-shaped connector, according to some embodiments.

Referring now to FIG. 4B, a connector 90 may include or correspond to the first connector 48 and/or the second connector 60 discussed with respect to FIGS. 2A-2B. In some embodiments, the connector 90 may not include any catch points for fluid or the instrument 80 moving through the connector 90 in the distal direction to enter the catheter adapter 32. In some embodiments, catch points similar to the catch points 24, illustrated in FIG. 1C, for example, may be removed from a fluid pathway between a proximal port and a distal port, or between the second port 52 and the third port

64 of FIGS. 2A-2B, for example. In some embodiments, the connector 90 may or may not include a wedge to eliminate the catch points.

Figure 5:
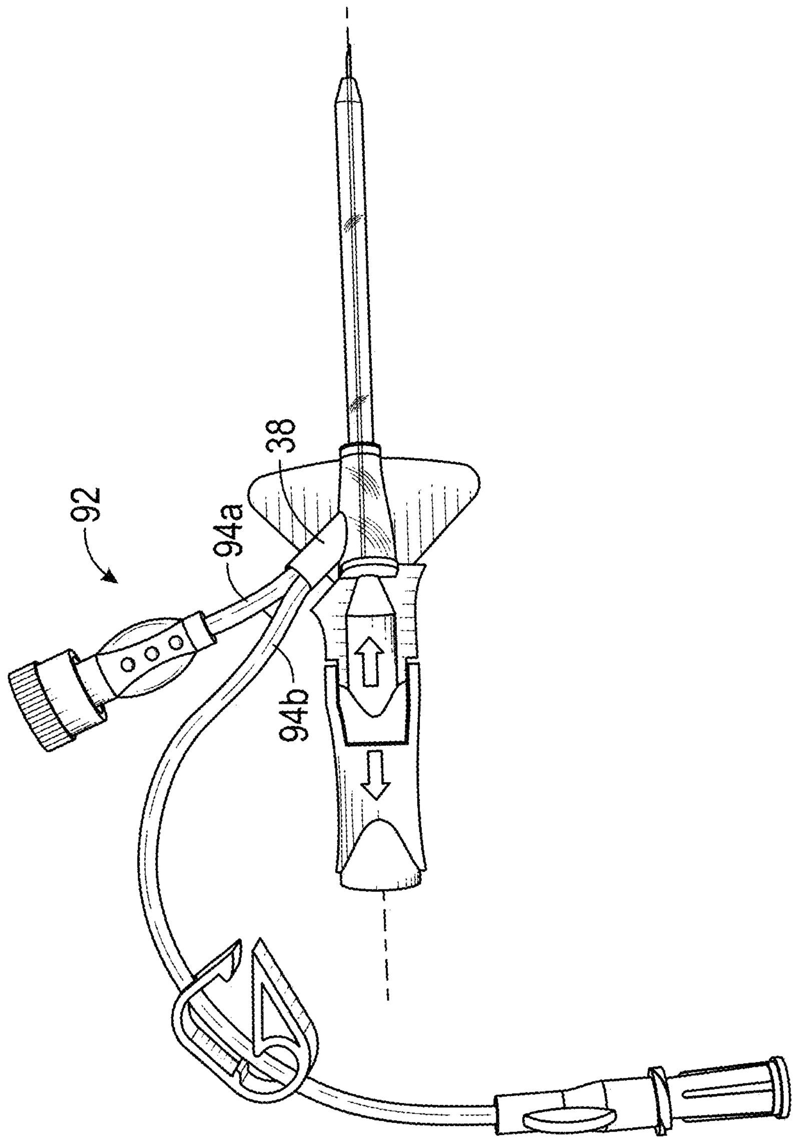
FIG. 5 is an upper perspective view of another catheter assembly, according to some embodiments.

Referring now to FIG. 5, in some embodiments, a catheter assembly 92 may include two or more extension tubes 94 extending from the side port 38. In some embodiments, a single extension tube may bifurcate or split into the extension tubes 94. In some embodiments, the bifurcation or splitting may occur within the side port 38 or outside of the side port 38. In some embodiments, the catheter assembly 92 may include or correspond to the prior art catheter assembly 10 discussed with respect to FIGS. 2A-2C. In further detail, in some embodiments, the catheter assembly 92 may include one or more features of the prior art catheter assembly 10 discussed with respect to FIGS. 2A-2C, such as, for example, the first connector 48 and/or the second connector 60. In some embodiments, one or more of the extension tubes 94 may include or correspond to the first extension tube 42 and/or the catheter assembly 92 may include multiple extension sets.

Figure 6A:
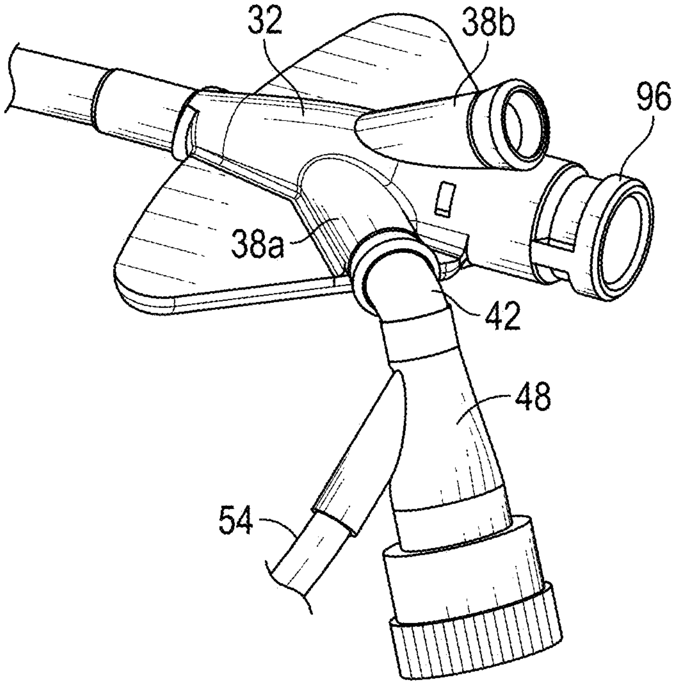
FIG. 6A is an upper perspective view of another example catheter adapter, according to some embodiments.
Figure 6B:
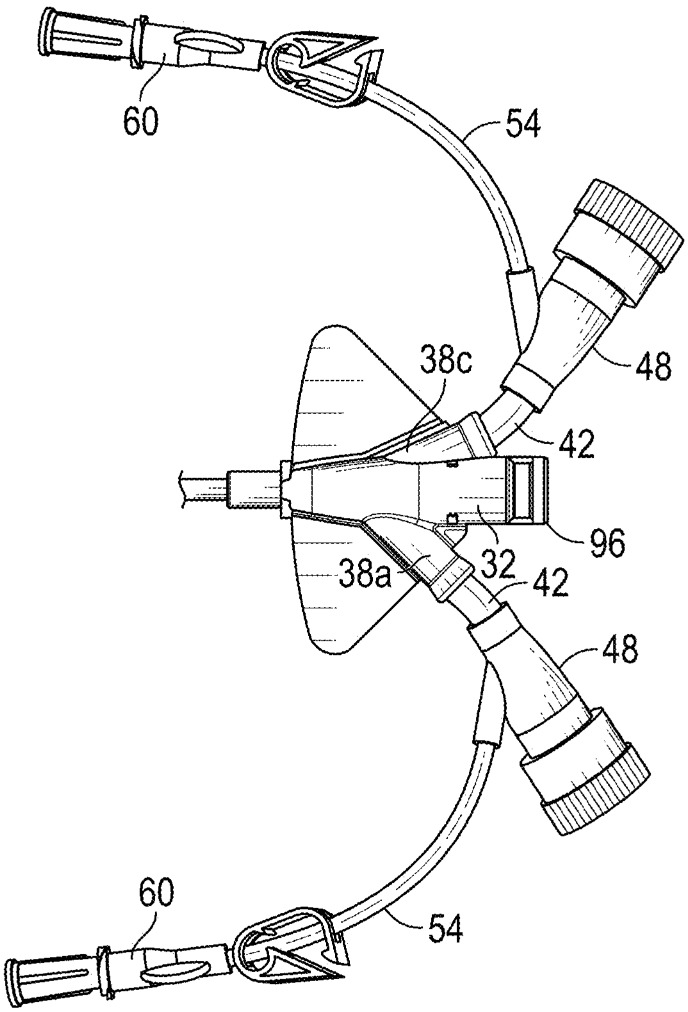
FIG. 6B is an upper perspective view of another example catheter adapter, according to some embodiments.

Referring now to FIG. 6A-6B, in some embodiments, the catheter adapter 32 may include various configurations. In some embodiments, the catheter adapter 32 may include multiple side ports 38. As illustrated in FIG. 6A, in some embodiments, a side port 38*a* may extend from a side of the catheter adapter 32 and/or another side port 38*b* may extend from a top of the catheter adapter 32. Additionally or alternatively, in some embodiments, another side port 38*c* may oppose the side port 38*a*. In some embodiments, the extension tubes 94 of FIG. 5 may extend from any of the side ports 18 of FIGS. 6A-6B. In some embodiments, all or a portion of the extension set of FIGS. 2A-2C may extend from any of the side ports 38 of FIGS. 6A-6B. In some embodiments, the first extension tube 42 described with respect to FIGS. 2A-2C may extend from any of the side ports 18 of FIGS. 6A-6B.

Figure 6C:
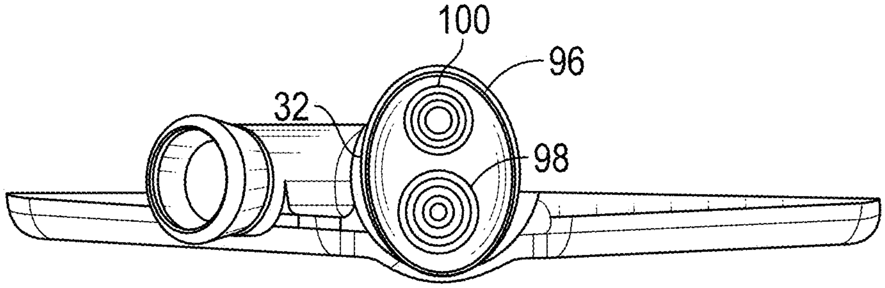
FIG. 6C is a proximal end view of another example catheter adapter, according to some embodiments.

Referring now to FIG. 6C, in some embodiments, a distal end 96 of the catheter adapter 12 may include a needle port 98 and/or a distal port 100 from which an extension tube, such as, for example, the first extension tube 42 of FIGS. 2A-2C may extend. In some embodiments, the extension tubes 94 of FIG. 5 may extend from the distal port 100. In some embodiments, the needle port 98 and the distal port 100 may be disposed vertically with respect to each other, as illustrated, for example, in FIG. 6C. In some embodiments, positioning of the distal port 100 towards a top of the catheter may facilitate entry of the instrument in to the catheter 40 and/or the vasculature of the patient at a downward angle. In some embodiments, the needle port 98 and the distal port 100 may be disposed horizontally with respect to each other.

Figure 7A:
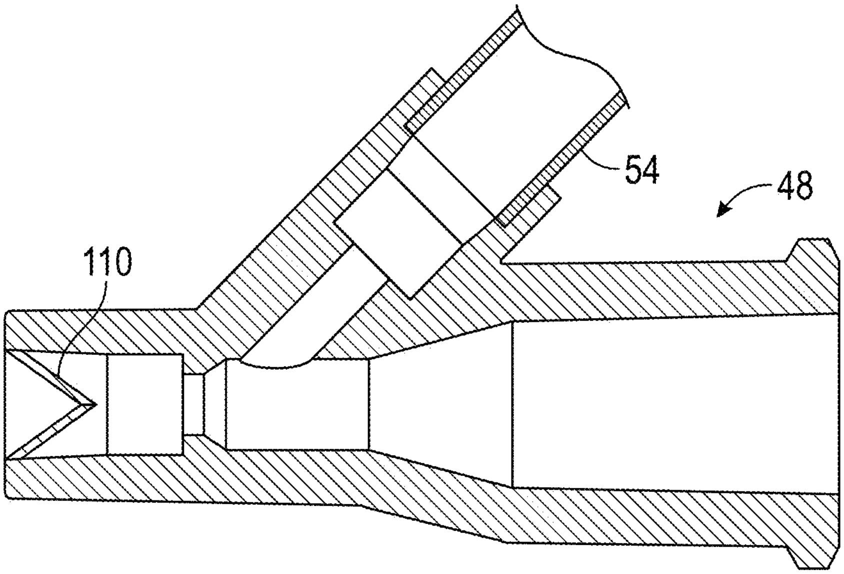
FIG. 7A is a cross-sectional view of another example Y-shaped connector, according to some embodiments.
Figure 7B:
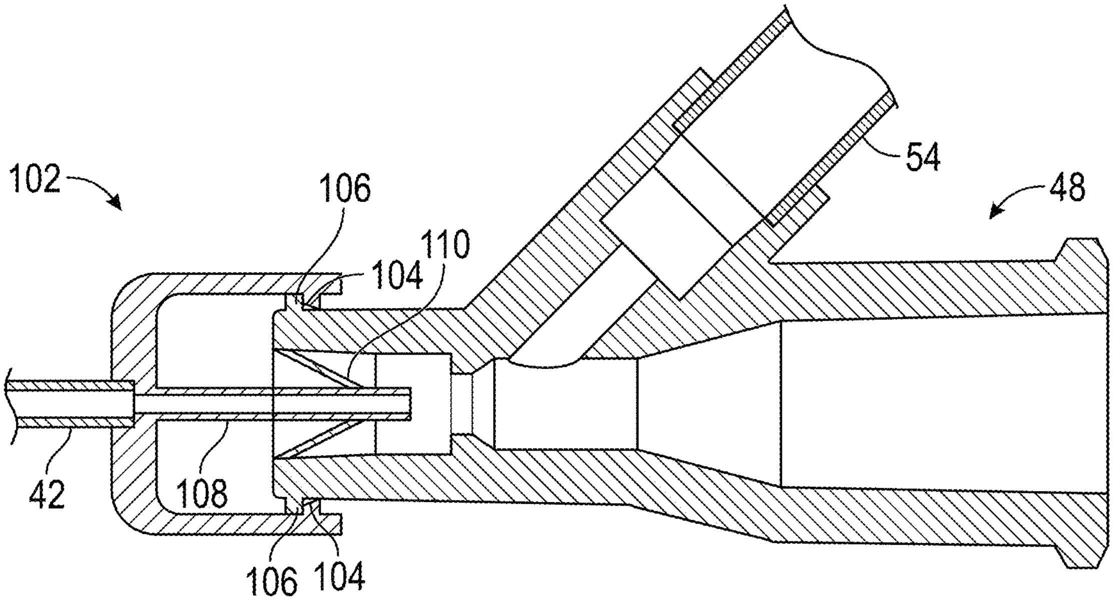
FIG. 7B is a cross-sectional view of the Y-shaped connector of FIG. 7A coupled to an example extension tube via a snap fit.

Referring now to FIGS. 7A-7B, in some embodiments, one or more components of the catheter assembly 30 described with respect to FIGS. 2A-2C may be coupled together via a snap fit. For example, as illustrated in FIGS. 7A-7B, a proximal end of the first extension tube 42 may include a snap mechanism 102 having snap elements 104 configured to move past corresponding snap elements 106 of the first connector 48 and engage the first connector 48 and the first extension tube 42 together in a snap fit. In some embodiments, a blunt cannula 108 may penetrate a blood control valve 110 of the first connector 48. It is contemplated that the first connector may include the blunt cannula 108.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A peripheral intravenous catheter assembly, comprising:

a catheter adapter comprising a proximal end, a distal end, a lumen extending through the proximal end and the distal end along a longitudinal axis of the catheter adapter, and a side port that extends outwardly and distally from a first side of the catheter adapter at a first acute angle from the longitudinal axis of the catheter adapter;

a catheter extending distally from the distal end of the catheter adapter;

a first extension tube comprising a proximal end and a distal end, wherein the first extension tube extends from the side port at the first acute angle, the first extension tube having a length between 10 and 14 millimeters;

a first connector comprising a first port, a second port at a proximal end of the first connector, a third port at a distal end of the first connector and opposite the second port, a lumen extending through the first port, the second port, and the third port, wherein the third port is coupled to the proximal end of the first extension tube to thereby position the third port between 10 and 14 millimeters from the side port, wherein the second port and the third port are aligned on a longitudinal axis of the first connector and the first port extends outwardly and distally from a first side of the first connector at a second acute angle from the longitudinal axis of the first connector, wherein the first and second acute angles are selected so that, when the longitudinal axis of the first connector is aligned with a longitudinal axis of the side port, the first port is substantially perpendicular to the longitudinal axis of the catheter adapter, the length of the first connector along the longitudinal axis of the first connector being between 0.5 and 0.6 inches;

a second extension tube comprising a proximal end and a distal end, wherein the distal end of the second extension tube is coupled to the first port, the second extension tube having a length between 4 and 7 inches; and a second connector coupled to the proximal end of the second extension tube, wherein the lengths of the first and second extension tubes and the first and second acute angles in combination are dimensioned and oriented such that the second connector is positioned distal to the catheter adapter to thereby minimize interference of the second connector with a hand of a clinician as the clinician grips the catheter adapter to insert the catheter into a vasculature of a patient;

wherein a portion of the lumen of the first connector does not include any catch points for a probe moving through the first connector in the distal direction, wherein the portion of the lumen of the first connector extends along the longitudinal axis of the first connector and through an entirety of the second port of the first connector to the first extension tube, wherein the lengths of the first connector and the first extension tube are configured to facilitate rapid infusion of medications into and instrument access to the vasculature of the patient via the first connector.

2. The peripheral intravenous catheter assembly of claim 1, wherein the first and second acute angles are each approximately 45°.

3. The peripheral intravenous catheter assembly of claim 1, wherein the first acute angle is greater than the second acute angle.

4. The peripheral intravenous catheter assembly of claim 1, wherein the first acute angle is less than the second acute angle.

5. The peripheral intravenous catheter assembly of claim 1, wherein the first and second acute angles are selected so that the first port is perpendicular to the longitudinal axis of the catheter adapter.

6. The peripheral intravenous catheter assembly of claim 1, wherein the first connector is coupled to the proximal end of the first extension tube via a snap fit.

7. The peripheral intravenous catheter assembly of claim 1, wherein the proximal end of the first extension tube is fixed within the first connector.

8. The peripheral intravenous catheter assembly of claim 1, further comprising a clamp disposed on the second extension tube.

9. The peripheral intravenous catheter assembly of claim 1, wherein the side port is a first side port, wherein the catheter adapter further comprises a second side port disposed on a top of the catheter adapter.

10. The peripheral intravenous catheter assembly of claim 1, wherein the side port is a first side port, wherein the catheter adapter further comprises a second side port opposing the first side port.

11. The peripheral intravenous catheter assembly of claim 10, further comprising:

a third extension tube comprising a proximal end and a distal end, wherein the third extension tube extends from the second side port;

a third connector coupled to the proximal end of the third extension tube, wherein the third connector comprises a third port and a fourth port;

a fourth extension tube comprising a proximal end and a distal end, wherein the distal end of the fourth extension tube is coupled to the third port, wherein the fourth extension tube is longer than the third extension tube; and a fourth connector coupled to the proximal end of the fourth extension tube.

12. A peripheral intravenous catheter assembly, comprising:

a catheter adapter comprising a proximal end, a distal end, a lumen extending through the proximal end and the distal end along a longitudinal axis of the catheter adapter, and a side port that extends outwardly from a first side of the catheter adapter at a first angle from the longitudinal axis of the catheter adapter;

a catheter extending distally from the distal end of the catheter adapter;

a first extension tube comprising a proximal end and a distal end, wherein the first extension tube extends from the side port at the first angle, the first extension tube having a length between 10 and 14 millimeters;

a first connector comprising a first port, a second port at a proximal end of the first connector, a third port at a distal end of the first connector and opposite the second port, a lumen extending through the first port, the second port, and the third port, wherein the third port is coupled to the proximal end of the first extension tube to thereby position the third port between 10 and 14 millimeters from the side port, wherein the second port and the third port are aligned on a longitudinal axis of the first connector and the first port extends outwardly from a first side of the first connector at a second angle from the longitudinal axis of the first connector, wherein the first and second angles are selected so that, when the longitudinal axis of the first connector is aligned with a longitudinal axis of the side port, the first port is oriented distally at an angle greater than 90° from the longitudinal axis of the catheter adapter, the length of the first connector along the longitudinal axis of the first connector being between 0.5 and 0.6 inches;

a second extension tube comprising a proximal end and a distal end, wherein the distal end of the second extension tube is coupled to the first port, the second extension tube having a length between 4 and 7 inches; and a second connector coupled to the proximal end of the second extension tube, wherein the lengths of the first and second extension tubes and the first and second angles in combination are dimensioned and oriented such that the second connector is positioned distal to the catheter adapter to thereby minimize interference of the second connector with a hand of a clinician as the clinician grips the catheter adapter to insert the catheter into a vasculature of a patient;

wherein the lengths of the first connector and the first extension tube are configured to facilitate rapid infusion of medications into and instrument access to the vasculature of the patient via the first connector.

13. The peripheral intravenous catheter assembly of claim 12, wherein the first angle is approximately 45° and the second angle is approximately 90°.

14. The peripheral intravenous catheter assembly of claim 12, wherein the first angle is approximately 45°.

15. The peripheral intravenous catheter assembly of claim 12, wherein the second angle is approximately 90°.

* * * * *